United States Patent [19]

Baranowitz

[11] Patent Number: 5,455,280
[45] Date of Patent: Oct. 3, 1995

[54] TREATMENT OF CHRONIC LYMPHOCYTIC LEUKEMIA WITH BETA-CAROTENE

[76] Inventor: Steven Baranowitz, 85 Tices La., East Brunswick, N.J. 08816

[21] Appl. No.: 166,622

[22] Filed: Dec. 13, 1993

[51] Int. Cl.⁶ .................................................. A61K 31/015
[52] U.S. Cl. .......................... 514/763; 514/766; 514/783; 514/908
[58] Field of Search .................................... 514/763, 766, 514/783, 789, 908

[56] References Cited

U.S. PATENT DOCUMENTS 5,008,295   4/1991   Nishino et al. ........................ 514/766

OTHER PUBLICATIONS

Harinder S. Garewal, et al. (1992) *Cancer Epidemiology, Biomarkers & Prevention*, vol. 1, pp. 155–159.
(Editorial) (1992) *Annals of Internal Medicine*, vol. 1, 117, No. 4, pp. 338–340.
Kenneth A. Foon, et al. (1992) *LEUKEMIA*, 6 Suppl. 4:26–32. pp. 26–32.
Dirck L. Dillehay, et al. (1989) *Cancer Research*, vol. 49, pp. 44–50.
I. Blazsek, et al. (1991) *Biomed & Pharmacother*, vol. 45, pp. 169–177.
Josephia R. F. Muindi, et al. (1992) *Cancer Research*, vol. 52, pp. 2138–2142.
John S. Bertram, et al. (1987) *Cancer Research*, vol. 47, pp. 3012–3031.
Gonul Hicsonmez, et al. (1991) *Leukemia Research*, vol. 15, No. 7, pp. 537–541.
P. Fenaux, et al. (1992) *LEUKEMIA*, vol. 6, Suppl. 1, pp. 64–66.
Sylvie Castaigne, et al. (1990) *Blood*, vol. 76, No. 9, pp. 1704–1709.
Raymond P. Warrell, Jr., et al. (1990) *New England Journal of Medicine*, vol. 324, pp. 1385–1393.
Stanley R. Frankel, et al. (1992) *Annals of Internal Medicine*, vol. 117, No. 4, pp. 292–296.
Laurence Detourmignies, et al. (1992) *Journal of Clinical Oncology*, vol. 10, No. 9, pp. 1430–1435.
B. A. Bell, et al. (1991) *Journal of Immunotherapy*, vol. 10, pp. 77–83.
Achary B. Kramer, et al., (1991) *CANCER*, vol. 67, No. 6, pp. 1484–1486.
Harry W. Findley, Jr., et al. (1984) *Experimental Hematology*, vol. 12, pp. 768–773.
Edo Hoting, et al. (1988) *CANCER*, vol. 62, No. 6, pp. 1044–1048.
Stephen J. Hoffman, et al. (1988) *American Journal of Hematology*, vol. 28, pp. 124–127.
Attilio Roveli, et al. (1992) *Journal of Clinical Oncology*, vol. 10, No. 9. pp. 1413–1418.
Mikio Furuse, et al. (1992) *Cellular Immunology*, vol. 143, pp. 298–309.

Arnold S. Freedman (1990) *Hematology/Oncology Clinics of North America*, vol. 4, No. 2, pp. 405–429.
Tin Han, et al. (1990) *Hematology/Oncology Clinics of North America*, vol. 4, No. 2, pp. 431–445 441–455.
Richard M. Stone (1990) *Hematology/Oncology Clinics of North America*, vol. 4, No. 2, p. 457.
Nancy Berliner (1990) *Hematology/Oncology Clinics of North America*, vol. 4, No. 2, pp. 473–487.
Michael J. Keating et al. (1992) *LEUKEMIA*, vol. 6, Supplement 4, pp. 140–141.
Ciril Rozman, et al. (1992) *LEUKEMIA*, vol. 6, Supplement 4, pp. 137–139.
Richard I. Edelson, M.D. (1992) *Yale University/Glaxo Dermatology Lectureship Series in Dermatology*, Lecture, pp. 4–16.
R. A. Krance, et al. (1992) *LEUKEMIA*, vol. 6, No. 4, pp. 251–255.
David F. Claxton, et al. (1992) *BLOOD*, vol. 80, No. 3, pp. 582–586.
S. Waxman, et al. (1992) *Biomed & Pharmacother*, vol. 46, pp. 183–192.
Mun–Fai Leung et al. (1992) *Leukemia Research*, vol. 16, No. 9, pp. 929–935.
J. Brice Weinberg, et al. (1992) *BLOOD*, vol. 79, No. 12, pp. 3337–3343.
Donald Pinkel, et al. (1992) *LEUKEMIA*, vol. 6, Supplement 2, pp. 127–131.
Olalekan Odeleye, et al. (1992) *Life Sciences*, vol. 51, pp. 129–134.
Seitetsu Sato, et al. (1992) *Anticancer Reserach*, vol. 12, pp. 371–376.
Masaaki Inaba, et al. (1992) *Archives of Biochemistry and Biophysis*, vol. 293, No. 1, pp. 181–186.
Martin S. Tallman et al. (1992) *BLOOD*, vol. 79, No. 3 pp. 543–553.
N. Takeichi, et al. *An LPS–Resistant Sublne of Rat Myelomonocytic Leukemia Acquires Organ–Affinity*, pp. 328–333.
Nancy L. Oliveira, et al., (1992) *BLOOD*, vol. 79, No. 3, pp. 627–633.
Craig Moskowitz, et al. (1992) *American Journal of Hematology*, vol. 39, pp. 102–107.
Robert Hast, et al. (1992) *Leukemia Research*, vol. 16, No. 1, pp. 95–100.

(List continued on next page.)

Primary Examiner—Nathan M. Nutter
Attorney, Agent, or Firm—Darby & Darby

[57] ABSTRACT

According to the present invention, there is provided a method for treating chronic lymphocytic leukemia (CLL) in a mammal. Beta-carotene is administered to the mammal in CLL therapeutically effective amounts. The invention also contemplates a method for treating T-cell chronic lymphocytic leukemia (T-CLL). T-CLL therapeutically effective amounts of beta-carotene are administered. In further embodiment, a method for lowering or maintaining the level of white blood cells in a mammal having chronic lymphocytic leukemia is provided. White blood cell therapeutically effective amounts of beta-carotene are administered to the mammal.

25 Claims, No Drawings

OTHER PUBLICATIONS

James R. Flanagan, et al. (1992) *Molecular and Cellular Biology*, vol. 12, No. 1, pp. 38"44.
Kun–Sang Chang, et al. (1992) *Molecular and Cellular Biology, vol. 12, No. 2, pp. 800–810.*
Kun–Sang Chang, et al. (1992) *BLOOD*, vol. 79, No. 3, pp. 554–558.
Daniel. W. Nebert, et al. (1979) *Biochemical Pharmacology*, vol 27, pp. 149–151.
Maria L. Duran–Reynals, et al. (1978) *The Journal of Experimental Medicine*, vol. 147, pp. 459–469.
Fabien Guidez, et al. (1991) *LEUKEMIA*, vol. 5, No. 8, pp. 699–703.
Daniel S. Cowen, et al. (1991) *Journal of Leukocyte Biology*, vol. 50, pp. 109–122.
A. Geurts van Kessel, et al. (1991) *Human Genetics*, vol. 87, pp. 201–204.
S. Smith (1971) *Am. Assoc. Cancer Res.*, vol. 12, p. 85.
Tsuyoshi Nakamaki, et al. (1990) *Leukemia Research*, vol. 14, No. 9, pp. 785–794.
Victoria L. Stevens, et al. (1990) *Cancer Research*, vol. 50, pp. 222–226.
Raymond J. Monnat, Jr. (1989) *Cancer Research*, vol. 49, pp. 81–87.
Ludwik Groos (1988) *CANCER*, vol. 62, No. 8, pp. 1463–1465.
Haruhiko Ohashi, et al. (1992) *LEUKEMIA*. vol. 6, No. 8, pp. 859–862.
S. Tohda, et al. (1992) *LEUKEMIA*, vol. 6, No. 7, pp. 656–661.
Jose R. Perez, et al. (1992) *Journal of Cellular Biochemistry*, vol. 50, pp. 26–34.
Jianming Li, et al. (1992) *Leukemia Research*, vol. 16, No. 6/7, pp. 571–576.
Eric K-W. Hui, et al. (1992) *Life Sciences*, vol. 51, pp. 415–422.
Eric K-W. Hui, et al. (992) *Experimental Hematology*, vol. 20, pp. 454–461.
Piotr Pierzchalsi, et al. (1992) *FEBS* 10732, vol. 298, No. 2,3, pp. 165–168.
S. Tohda, et al. (1991) *LEUKEMIA*, vol. 5, No. 11, pp. 951–957.
N. Takahashi et al., *Retinoic Acid Acylation*, pp. 255–264.
Josephia Muindi, et al. (1992) *BLOOD*, vol. 79, No. 2, pp. 299–303.
V. Santini, et al. (1991) *Leukemia Research*, vol. 15, No. 5, pp. 341–350.*Editorial* (1991) *Leukemia Research*, vol. 15, No. 8, pp. 655–657.
Peter H. Wiernik, et al. (1991) *LEUKEMIA*, vol. 5, No. 6, pp. 504–509.
Kosei Takeuchi, et al. (1991) *Biochemical and Biophysical Research Communications*, vol. 178, No. 1 pp. 263–268.
Kent A. Robertson, et al. (1991) *BLOOD*, vol. 77, No. 2, pp. 340–347.
Alam et al. (1990) *Nutrition and Cancer*, vol. 14, No. 2, pp. 111–116.
Akiko Sakashita, et al. (1991) *LEUKEMIA*, vol. 5, No. 1, pp. 26–31.
Yuhei Hamasaki, et al. (1991) *Biochimica et Biophysica Acta*, vol. 1082, pp. 126–129.
Carlo Aul, et al. (1992) *Leukemia Research*, vol. 16, No. 3, pp. 207–215.
Theodore R. Breitman, et al. (1990) *Cancer Research*, vol. 50, pp. 6268–6273.
Tsuyoshi Nakamaki, et al. (1989) *Jpn. J. Cancer Res.*, vol. 80, pp. 1077–1082.
Steven J. Collins, et al. (1990) *Molecular and Cellular Biology*, vol. 10, No. 5, pp. 2154–2163.
Chi-Kuan Ho, et al. (1989) *Differentiation*, vol. 40, pp. 70–75.
F. Serri, et al. (1990) *Current Problems in Dermatology*, vol. 19, pp. 252–257.
Kun–Sang Chang, et al. (1991) *LEUKEMIA*, vol. 5, No. 3, pp. 200–204.
Takehiko Nakamura, et al. (1988) *Eur. J. Haematol*, vol. 41, pp. 258–266.
Robert E. Gallagher, et al. (1989) *LEUKEMIA*, vol. 3, No. 11, pp. 789–795.
Xingzhong Wu, et al. (1989) *Leukemia Research*, vol. 13, No. 10, pp. 869–874.
Masue Imaizumi, et al. (1988) *Cancer Research*, vol. 48, No. 13, pp. 6733–6738.
Wilson H. Miller, Jr., et al. (1992) *Proc. Natl. Acad. Sci. USA*, vol. 89, pp. 2694–2698.
Degos, L. et al., Saurat J–H (ed): Retinoids: 10 Years On. Basel, Karger, 1991, pp. 121–126.
Cornic, M., et al. (1992) *Bull Cancer*, vol. 79, pp. 697–704.
Philippe Kastner, et al. (1991) *C.R. Soc. Biol.*, vol. 185, pp. 391–401.
Mokady et al. (1991) *Nutrution and Cancer*, vol. 15, No. 1, pp. 47–52.
Dimitrov et al. (1990) *Chemistry & Biology*, pp. 269–277.
Runde et al. (1992) *Blood*, vol. 79. No. 2, pp. 53–535.

TREATMENT OF CHRONIC LYMPHOCYTIC LEUKEMIA WITH BETA-CAROTENE

FIELD OF THE INVENTION

The invention relates to a method for the treatment of chronic lymphocytic leukemia (CLL) in mammals. Beta carotene is administered, preferably systemically, in a therapeutically effective amount. The administration of beta-carotene has been found to be particularly effective in the treatment of T-cell chronic lymphocytic leukemia (T-CLL) and in the lowering of abnormal white blood cell levels in patients suffering from T-CLL.

BACKGROUND OF THE INVENTION

CLL involves the proliferation of neoplastic peripheral blood lymphocytes. About 95 percent of CLLs express surface antigens which indicate they are of B-cell origin, while the remaining 5 percent are of T-cell origin.

CLLs of different origins have different clinical presentations and general disease courses. B-cell CLLs generally infiltrate the lymph nodes, bone marrow, and spleen and tend to have a indolent course. In contrast, T-cell CLLs are more malignant/and present additional infiltration in the skin (Freedman et al., *Hematol. Oncol. Clinics of N. Am.* 4(2):405–456, 1990).

Treatment of CLL is generally individualized. No specific treatment is required in older patients having an indolent form of the disease. However, other patients with more advanced disease or with disease having a more rapid course may have a median survival of less than two years. Therefore, some sort of treatment should be pursued. The majority of patients have an intermediate prognosis, and although they fare reasonably well without treatment for several years, ultimately they will require some form of therapy.

The typical treatment for CLL is the administration of chlorambucil, a chemotherapeutic agent. Combination chemotherapy is generally used only in advanced cases. Radiation therapy has been effectively used, particularly if splenic enlargement is present and bone marrow transplantation has been successful with younger patients (Foon et al., *Leukemia* 6(Supp. 4):26–32, 1992). More recently, the nucleoside fludarabine, a fluorinated adenine analog, and 2-chlorodeoxyadenosine, a deoxyadenosine analog, have been found to be effective. Both analogs are resistant to deamination (Keating et al., *Leukemia* 6(Supp. 4):140–141, 1992). All of these therapies focus on elimination (with replacement, in the case of the transplants) of the malignant cells.

Differentiation treatment has been developed for the treatment of leukemias of immature cells, such as acute promyelocytic leukemia (APL). Rather than killing the malignant cells, factors which cause the cells to mature are administered, and as a result, the malignant immature cells mature and lose their neoplastic nature.

It has been found that retinoids, and particularly trans-retinoic acid, are effective in treating APL (Warrell et al. *New Eng. J. Med.* 324:1385–1393, 1991). The treatment of pediatric acute nonlymphocytic leukemia (ANLL) (Bell et al. *J. of Immunother.* 10:77–83,1991), acute myeloid leukemia (AML) in elderly patients (Kramer et al. *Cancer* 67(6):1484–1486, 1991), and cutaneous T- cell lymphoma (CTCL) (Hoting et al. *Cancer* 62(6):1044–1048, 1988) with forms of retinoic acid and its analogs has been the subject of clinical studies. However, neither retinoids nor carotinoids such as beta-carotene have been used in the treatment of leukemias involving mature cells, such as with CLL or T-CLL.

Other studies of the use of retinoids and carotinoids in the prevention of various types of cancer have been reported (see, for example, Table 3 of Bertram et al., *Cancer Res.* 47:3012–3031, 1987). However, these studies have generally concentrated on cancers of the digestive or reproductive systems and do not discuss the treatment of leukemia. For example, Garewal et al., *Can. Epid. Biomark. Prev.* 1:155–159, 1992, proposed to treat leukoplakia with vitamin A in combination with beta-carotene.

It has now been discovered that beta-carotene therapy is effective in the treatment of established mature cell malignancies such as CLL and T-CLL.

SUMMARY OF THE INVENTION

According to the present invention, there is provided a method for treating chronic lymphocytic leukemia in a mammal. In this embodiment, CLL therapeutically effective amounts of beta-carotene are administered.

The invention also contemplates a method for treating T-cell chronic lymphocytic leukemia in a mammal. Beta-carotene is administered in T-CLL therapeutically effective amounts.

In a further contemplated embodiment, a method for lowering or maintaining the level of white blood cells in a mammal having chronic lymphocytic leukemia is provided. White blood cell therapeutically effective amounts of beta-carotene are administered to the mammal.

DETAILED DESCRIPTION OF THE INVENTION

Carotinoids are terpenes that are widely distributed in the plant and animal kingdoms. Beta-carotene is a common carotenoid having the chemical structure:

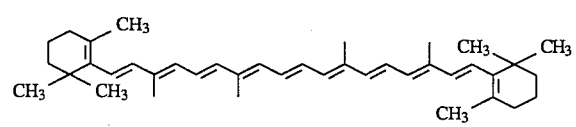

Beta-carotene readily undergoes oxidated cleavage at the central double bond to give two equivalents of the aldehyde retinol in mammals. Biochemical reduction of the aldehyde carbon yields vitamin A.

Chronic lymphocytic leukemia is described in The Merck Manual of Diagnosis and Therapy, 15th Ed. Merck, Sharp & Dohme Research Laboratories (1987) as a clonal expansion of mature-appearing lymphocytes and involves lymph nodes and other lymphoid tissues with progressive infiltration of bone marrow and circulation in blood. It is two to three times more common in males than in females. Clonal expansion in most CLL patients is by cells with B-lymphocyte characteristics and surface immunoglobulin (SIg). The clonal SIg is usually IgM in type with either kappa or lambda light chains. In a few patients, the SIg is of the IgG variety, again with either kappa or lambda light chains. Less than 5 percent of all CLL patients have lymphocytes with T-cell characteristics.

The accumulation of lymphocytes is believed to begin in the lymph nodes, but spreads to other lymphoid tissues. The liver and spleen may become involved as well. Abnormal hematopoiesis results in anemia, agranulocytosis, and thrombocytopenia. There are immunoregulatory problems involving immunoglobulin production.

Most patients develop hypogammaglobulinemia and impaired antibody response. In some patients, this appears to be related to increased activity of T-suppressor cells. Skin infiltration may be a feature of T-cell CLL.

Laboratory findings of patients disclose a sustained, absolute lymphocytosis (greater than 5,000/microliter) and an increase of lymphocytes in the bone marrow.

Present treatments for CLL include red blood cell transfusion for anemia, platelet transfusions for bleeding associated with thrombocytopenia, and antibiotics for bacterial infections. Additionally, irradiation, antineoplastic drugs, and corticosteroids may be administered. However, treatments do not prolong survival and may be associated with significant side effects. Furthermore, overtreatment can be more dangerous than undertreatment.

In all of the embodiments of the present invention, beta-carotene is preferably administered systemically. Systemically is meant to define all methods of administration other than topical. Systemic administration most preferably is by the oral route.

A daily dosage identifies the average amount of beta-carotene administered to an individual. However, the dosage need not be administered daily. The daily dosage is merely an average dosage that a patient receives when beta-carotene is administered over a period. The daily dosage can be administered in divided portions so that the total amount administered is the daily dosage.

Beta-carotene is a component of the normal diet of most mammals, and the recommended daily requirement of beta-carotene for a normal adult human is about 3 mg. Although beta-carotene is provided through normal diet, the amounts of beta-carotene useful in the present invention typically cannot be provided by normal diet. This is because the foods that supply beta-carotene in a normal diet contain various other substances. If sufficient amounts of these foods were consumed to provide the necessary amounts of beta-carotene, these other substances would be consumed in toxic amounts. Furthermore, approximately 25–75 percent of the carotinoids consumed by normal diet are not absorbed and are excreted in the feces relatively unchanged. Therefore, beta-carotene is supplied in the methods of the present invention through supplementation. Commercially available forms of beta-carotene are available, for example, from Hoffman-LaRoche under the trademark SOLATENE® or as beta-carotene.

Although the safe upper limit of the amount of beta-carotene that can be administered to a human has not yet been determined, it is believed that such an upper limit is at least 1000 mg/day. Typically, acceptable blood levels of beta-carotene and chemically detectable changes in blood levels would be achieved after administration of beta-carotene in the prescribed amounts for several weeks.

In the treatment of CLL, beta-carotene is administered in a CLL therapeutically effective amount. CLL therapeutically effective amounts of beta-carotene are those amounts sufficient to slow, or halt the progression of the disease or to resolve the symptoms of CLL. This amount will depend upon the age, weight, sex, sensitivity, and the like of the individual. The CLL therapeutically effective amount can be determined by experimentation well known in the art such as establishing a matrix of dosages and frequencies and assigning a group of experimental subjects to each point in the matrix. That amount will be a safe non-toxic amount. Typically, for a human being, that amount will be at least about 50/day of beta-carotene and preferably at least about 60 mg/day. Most preferably, that amount will range from about 60 mg/day to about 350 mg/day. Particularly, the dosage will be at least about 120 mg/day and, most particularly, about 300 mg/day.

The amount of beta-carotene required to treat T-CLL is a T-CLL therapeutically effective amount of beta-carotene. Again, this amount will depend upon the age, weight, sex, sensitivity, and the like of the individual. This amount can be determined experimentally as explained above. That amount will be a safe non-toxic amount. Typically, for an adult human being that amount will be at least about 50 mg/day and preferably at least about 60 mg/day. Most preferably, that amount will range from about 60 mg/day to about 350 mg/day. Particularly, the dosage will be at least about 120 mg/day and, most particularly, about 300 mg/day.

Typically, the white blood cell count in a normal, healthy human adult ranges from about 4,100 to about 10,300/microliter. Often, individuals affected with CLL or T-CLL have higher than normal white blood cell levels as determined by white blood cell count.

The aspect of the present invention directed to decreasing or maintaining white blood cell levels contemplates white blood cell levels as defined by white blood cell count. Elevated levels of white blood cells are those levels above levels for normal, healthy individuals described above. Lowering white blood cell levels indicates lowering these levels from any levels which are above normal levels, but lowering does not necessarily indicate that those levels are returned to normal levels.

The amounts of beta-carotene useful for lowering or maintaining white blood cell levels in a human having elevated white blood cell levels and particularly where in the elevation it is due to CCL or T-CCL are white blood cell therapeutically effective amounts. This amount also depends independently upon the age, weight, sex, sensitivity, medical condition, including, but not limited to the stage of disease, and the like of the individual, but can be determined experimentally as explained above. That amount will be a safe, non-toxic amount. Typically, for an adult human, that amount will be at least about 50 mg/day, and preferably at least about 60 mg/day. Most preferably, that amount will range from about 60 mg/day to about 350 mg/day. Particularly, the dosage will be at least about 120 mg/day, and most particularly, about 300 mg/day.

Beta-carotene administration in any of the methods of the present invention can be accompanied by the administration of a beta-carotene absorption enhancing adjuvant in a beta-carotene absorption enhancing amount. Such adjuvants include, but not limited to, safflower oil, bile salts, lipids, proteins, antioxidants, zinc, or any combination thereof. See, for example, Alam et al., "Influence of Dietary Fats and Vitamin E on Plasma and Hepatic Vitamin A and B-carotene levels in Rats Fed Excess B-carotene", *Nutrition and Cancer* 14: 2, 111–116 (1990); Mokady et al., "Dietary Lipid Level and the Availability of B-carotene of *Dunaliella-bardawil* Rats", *Nutrition and Cancer* 15 (1): 47–52 (1991); Dimitrov et al., "Bioavailibility of Carotenoids, *Carotenoids: Chemistry and Biology,* 269–277, Plenum Press (1990). Typically, for a solid dosage form, the amount of adjuvant will range from about 15 percent of to about four times the amount of beta-carotene. Typically, in a dietary supplement, the amount of adjuvant will range from about 2 to about 20 grams/day, preferably between about 10 and 20 grams/day, and most preferably between about 12 and 16 grams/day.

Adjuvant administration can precede, be concurrent with, follow, or any combination thereof, beta-carotene administration. Furthermore, beta-carotene administration can accompany the administration of other therapeutics that may be used in the treatment of CLL or T-CLL.

Because of the minimal side effects of beta-carotene, beta-carotene administration can continue for extended periods of time, and even for the lifetime of the individual, in order to maintain any therapeutic effects. Any decrease in white blood cell levels or any alleviation of any symptoms of CLL or T-CLL pursuant to the use of beta-carotene as set forth herein is within the scope of the present invention.

DESCRIPTION OF THE PREFERRED EMBODIMENTS

The following examples illustrate the invention without limitation.

EXAMPLE 1

A 65 year old male caucasian patient was diagnosed as having chronic lymphocytic leukemia and an associated cutaneous T-cell lymphoma. Intractable itching was observed due to the lymphoma. The patient was taking cardizem, a heart medication, for a heart attack, and occasionally, ativan for depression. He had been taking these medications for many years and was on no other oral medications. The patient had used a variety of topical medications, including various topical steroids prior to examination.

Physical examination revealed scattered erythematous macules (non-raised areas of redness). The patient was initially diagnosed about five years prior to beta-carotene treatment as having chronic lymphocytic leukemia Stage I (Rai classification). Skin biopsies one and three years prior to treatment with beta-carotene were reported as consistent with cutaneous T-cell lymphoma. Four years prior to beta-carotene treatment, the patient developed a whole body rash which was considered consistent with cutaneous T-cell lymphoma. The patient was treated with light which caused blistering. The patient was also treated with prednisone, psoralen and ultraviolet A irradiation, photophoresis (extracorporeal ultraviolet radiation of sensitized leukocytes), and ultraviolet B irradiation. Neither the lymphoma nor the associated intractable pruritis were successfully treated.

Blood tests, including quantitative lymphocyte studies, were performed four years and four months after initial diagnosis.

The patient was started on 300 mg of beta-carotene per day. During this period, the patient also received topical steroids for itching. Blood analyses were performed periodically. Results are illustrated in Table I.

TABLE 1

| | Blood Counts | | | | | | | | | | |
|---|---|---|---|---|---|---|---|---|---|---|---|
| | PRIOR TO BC TREATMENT | | | | | | BC TREATMENT | | | | |
| TIMELINE | 4 Years, 7 months | 4 Years, 6 Months | 2-3 Years | 1 Year | 5 weeks | 1 week | Day 1 | Day 44 | Day 52 | Day 85 | |
| DISEASE EVENT PERIOD | Prior to Diagnosis | Diagnosis | Conventional Therapy Failure | Stable on no treatment | Stable on no treatment | Just Prior to BC Treatment | | | | | |
| LABORATORY TEST | | | | | | | | | | | Normal Values |
| WHITE BLOOD CELLS | 27,900 | 28,800 | Fluctuation | 22,000 | 21,100 | 22,000 | | 16,300 | 15,500 | 15,500 | 4100–10300 |
| TOTAL LYMPHOCYTE | | | | | | 8,600 | | 7,700 | 6,400 | 5,300 | 700–4500 |
| T-HELPER (CD4) | | | | | | 8,273 | | | 6,105 | 5,061 | 359–1519 |
| T-SUPPRESSOR (CD8) | | | | | | 17 | | | 6 | 15 | 109–897 |
| B (CD19) | | | | | | 189 | | | 89 | 137 | <540 |

The data display a remarkable decrease in the patient's white blood cells due to the remission of T-cell lymphocytosis. It is not expected that the topical steroids were absorbed systemically or could have contributed to the patient's improvement. Furthermore, systemic steroids are known to typically increase leukocytosis initially during treatment rather than to decrease it.

The above-mentioned patents, test methods, and publications are hereby incorporated by reference.

Many variations of the present invention will suggest themselves to those skilled in the art in light of the above detailed description. All such obvious variations are within the full intended scope of the appended claims.

I claim:

1. A method for treating chronic lymphocytic leukemia (CLL) in a mammal, said method comprising administering to said mammal a CLL therapeutically effective amount of beta-carotene.

2. A method as defined in claim 1, wherein said CLL therapeutically effective amount of beta-carotene comprises from about 60 mg/day to less than a toxic amount.

3. A method as defined in claim 2, wherein said CLL therapeutically effective amount of beta-carotene comprises from about 60 mg/day to about 350 mg/day.

4. A method as defined in claim 3, wherein said CLL therapeutically effective amount of beta-carotene comprises about 300 mg/day.

5. A method as defined in claim 1, wherein said administering is systemic.

6. A method as defined in claim 5, wherein said administering is oral.

7. A method as defined in claim 1, further comprising concurrently or sequentially administering a beta-carotene absorption enhancing amount of a beta-carotene absorption enhancer.

8. A method as defined in claim 6, wherein said beta-carotene absorption enhancer comprises safflower oil.

9. A method of treating T cell chronic lymphocytic leukemia (T-CLL) in a mammal, said method comprising administering to said mammal a T-CLL therapeutically effective amount of beta carotene.

10. A method as defined in claim 9, wherein said T-CLL therapeutically effective amount of beta-carotene comprises from about 60 mg/day to less than a toxic amount.

11. A method as defined in claim 10, wherein said T-CLL therapeutically effective amount of beta-carotene comprises from about 60 mg/day to about 350 mg/day.

12. A method as defined in claim 11, wherein said T-CLL therapeutically effective amount of beta-carotene comprises about 300 mg/day.

13. A method as defined in claim 9, wherein said administering is systemic.

14. A method as defined in claim 13, wherein said administering is oral.

15. A method as defined in claim 9, further comprising concurrently or sequentially administering a beta-carotene absorption enhancing amount of a beta-carotene absorption enhancer.

16. A method as defined in claim 15, wherein said beta-carotene absorption enhancer comprises safflower oil.

17. A method for lowering or maintaining the level of white blood cells in a mammal having chronic lymphocytic leukemia, said method comprising administering to said mammal, a white blood cell therapeutically effective amount of beta-carotene.

18. A method as defined in claim 17, wherein said white blood cell therapeutically effective amount of beta-carotene comprises from about 60 mg/day to less than a toxic amount.

19. A method as defined in claim 18, wherein said white blood cell therapeutically effective amount of beta-carotene comprises from about 60 mg/day to about 350 mg/day.

20. A method as defined in claim 19, wherein said white blood cell therapeutically effective amount of beta-carotene comprises about 300 mg/day.

21. A method as defined in claim 17, wherein said administering is systemic.

22. A method as defined in claim 20, wherein said administering is oral.

23. A method as defined in claim 17, further comprising concurrently or sequentially administering a beta-carotene absorption enhancing amount of a beta-carotene absorption enhancer.

24. A method as defined in claim 23, wherein said beta-carotene absorption enhancer comprises safflower oil.

25. A method as defined in claim 15, wherein said mammal has a white blood cell level that is above normal levels due to chronic lymphocytic leukemia.

* * * * *